United States Patent [19]

Crispoldi et al.

[11] Patent Number: 4,874,595
[45] Date of Patent: Oct. 17, 1989

[54] PROCESS FOR PRODUCING CALCIUM-UREA NITRATE

[75] Inventors: Antonio Crispoldi; Andrea Moriconi, both of Terni; Mario Chiappafreddo, Amelia, all of Italy

[73] Assignees: Enichem Agricoltura S.p.A., Palermo; CCM S.r.l., Amelia; Tecnocentro S.r.l., Terni, all of Italy

[21] Appl. No.: 152,854

[22] Filed: Feb. 5, 1988

[30] Foreign Application Priority Data

Feb. 13, 1987 [IT] Italy .................. 19363A/87

[51] Int. Cl.$^4$ ............................... C06B 1/04
[52] U.S. Cl. ........................... 423/397; 71/58
[58] Field of Search ............ 71/58; 423/395, 396, 423/397

[56] References Cited

U.S. PATENT DOCUMENTS

| | | | |
|---|---|---|---|
| 1,776,694 | 9/1930 | Luscher | 71/58 |
| 1,840,229 | 1/1932 | Hamprecht | 423/395 |
| 1,916,617 | 7/1933 | Jaenecke et al. | 71/58 |
| 1,952,849 | 3/1934 | Eyer et al. | 71/58 |
| 3,342,578 | 9/1967 | Harshman et al. | 71/58 |
| 3,475,132 | 10/1969 | Seifert et al. | 71/58 |

FOREIGN PATENT DOCUMENTS

| | | | |
|---|---|---|---|
| 3146015 | 12/1982 | German Democratic Rep. | 71/58 |
| 199851 | 7/1967 | U.S.S.R. | 423/395 |

Primary Examiner—John Doll
Assistant Examiner—Wayne A. Langel
Attorney, Agent, or Firm—Oblon, Fisher, Spivak, McClelland & Maier

[57] ABSTRACT

Calcium-urea nitrate $[Ca(NO_3)_2 \cdot 4CO(NH_2)_2]$ is produced by means of a process, according to which:

a liquid composition is prepared, at a temperature not higher than 170° C., which contains urea and calcium nitrate, in a molar ratio to each other equal to, or approximately equal to, 4/1, and having a water content comprised within the range of from 0 to 15% by weight;

said liquid composition is sprayed, through a spray nozzle, on previously formed solid particles of calcium-urea nitrate, kept moving at a temperature comprised within the range of from 40° to approximately 100° C., and under a stream of an inert gas;

calcium-urea nitrate is recovered from said solid products from the spray.

The so obtained calcium-urea nitrate is in the form of a granular and free-flowing solid, free from the tendency to form dusts, and is useful in agriculture as a nitrogenous fertilizer.

Also the suitable equipment for carrying out the process of calcium-urea nitrate preparation as a continuous process is disclosed.

14 Claims, 1 Drawing Sheet

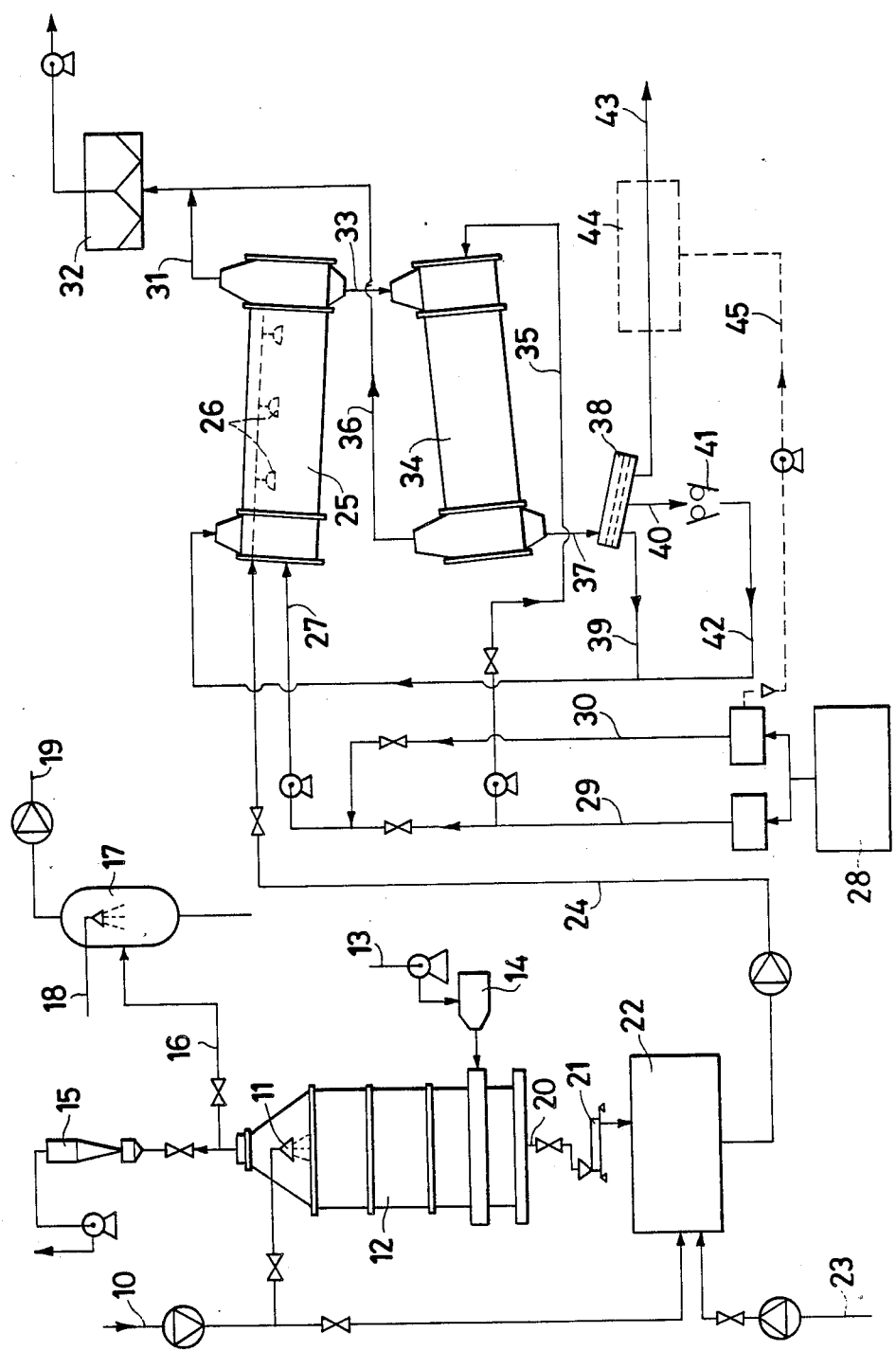

PROCESS FOR PRODUCING CALCIUM-UREA NITRATE

The present invention relates to a process for producing calcium-urea nitrate in the form of a granular and free-flowing solid, free from the tendency to release dusts, and useful in agriculture as a nitrogenous fertilizer. The invention relates also to the equipment for carrying out the same process, as a continuous process.

Calcium-urea nitrate is a per se known compound, and is a double salt of calcium and urea nitrate, wherein calcium nitrate constitutes approximately 40.6% by weight, and urea 59.4% by weight, and can be therefore defined by means of the formula:

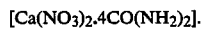

$[Ca(NO_3)_2 \cdot 4CO(NH_2)_2]$.

Such a double salt can be obtained e.g., as a crystalline precipitate from an over-saturated aqueous solution of calcium nitrate and urea nitrate.

Calcium-urea nitrate is potentially very interesting for use as a fertilizer, in that in addition to urea nitrogen, it contains nitric nitrogen which makes it possible, among others, the ammonia losses, typical for urea alone, when it undergoes the hydrolysis process in the soil, to be prevented.

In spite of that, heretofore calcium-urea nitrate has not found a meaningful commercial success, above all due to the difficulties to be faced when this product has to be given the suitable physical characteristics for it to be used as an agricultural fertilizer.

For example, calcium-urea nitrate processing by means of crystallization, prilling and granulation by the rotary-disk method do not make it possible a granular, free-flowing product, free from the tendency to form dusts, to be obtained.

In the art, also a fluid-bed processing was proposed, that involves operating difficulties, and the use of complex equipment.

However, the product which can be obtained by means of such a process contains an excess amount of urea as compared to the amount required for forming the double salt, and such a product suffers from the undesirable characteristic deriving from the low hardness values of the granules.

Finally, to date, the formation of calcium-urea nitrate, as a granular solid, by starting from the relevant precursors in the molten state, did not find a satisfactory solution, above all when the difficulties deriving from undermelting phenomena are taken into due account.

The purpose of the present invention is overcoming the above-said drawbacks in calcium-urea nitrate preparation.

More particularly, a purpose of the present invention is a simple and advantageous method for preparing calcium-urea nitrate in the form of freeflowing granules, endowed with excellent mechanical characteristics.

Another purpose of the present invention is constituted by the equipment for accomplishing said process as a continuous process.

Further purposes of the invention will be clear from the following disclosure.

According to the present invention, calcium-urea nitrate is prepared in the form of a granular and free-flowing solid, free from the tendency to form dust, by means of a process according to which:

a. a liquid composition is prepared, at a temperature not higher than 170° C., which contains urea nitrate and calcium nitrate, in a molar ratio to each other equal to, or approximately equal to, 4/1, and having a water content comprised within the range of from 0 to 15% by weight;

b. said liquid composition is sprayed, through a spray nozzle, on previously formed solid particles of calcium-urea nitrate, kept moving at a temperature comprised within the range of from 40° to approximately 10020 C., and under a stream of an inert gas;

c. calcium-urea nitrate is recovered from said solid products from the spray.

The sole FIGURE of the Drawing represents a flow diagram of the process for preparing calcium -urea nitrate according to the process of the present invention.

In the preferred form of practical embodiment, the (a) step is run at a temperature comprised within the range of from 100° to 170° C., with a water content in the composition comprised within the range of from 0 to 8% by weight. Furthermore, in the (b) step the calcium-urea particles are kept moving at a temperature preferably comprised within the range of from 40° to 75° C., and under conditions of cooling under the influence of a stream of an inert gas, in particular of air.

In the preparation of the liquid composition of the (a) step, calcium nitrate in the form of a dry powder or in the form of a partially de-hydrated powder, or in the form of a concentrated aqueous suspension having a water content of up to values of the order of from 15 to 18% by weight, can be used.

Furthermore, used calcium nitrate can contain ammonium nitrate as an impurity, up to levels of the order of from 5 to 6% by weight.

Ureas used in the liquid preparation of the (a) step normally shows a titer of the order of approximately 97% by weight or more, and may contain biuret as an impurity, with biuret amounts ranging up to approximately 1.2% by weight.

The process of preparation of the liquid composition is usually carried out by adding to molten urea calcium nitrate in the form of a dry powder, or in the form of partially dehydrated powder, or in the form of a concentrated aqueous suspension. Water in the composition, if present, can be adjusted within the above specified range of values, by means of the supply of water by calcium nitrate, and/or by urea and/or means of the direct addition to the same mixture. The temperature at which the liquid composition is formed may generally vary within the range of from 100° to 170° C. Above 170° C., the undesired phenomenon of the release of ammonia fumes due to reactions of decomposition may occur. At temperatures lower than 100° C., phenomena of solidification of the mass may occur.

The time necessary for calcium nitrate dissolving into molten urea varies as a function of temperature, of the physical characteristics of calcium nitrate, and of the water content of the medium inside which the process is run.

Normally, when such an equipment is used, which makes it possible molten urea and calcium nitrate to be efficaciously homogenized, the dissolving time is of the order of from 3 to 5 minutes.

The necessary time for calcium-urea nitrate to form is practically equal to the time of calcium nitrate dissolving into molten urea.

The reaction of formation of calcium-urea nitrate is exothermic, and in the absence of a cooling, causes an increase in the temperature of the mass of the order of 10° C.

It was observed that the speed of formation of biuret, when urea is combined with calcium nitrate in calcium-urea nitrate, is considerably lower that the formation speed in urea alone.

Therefore, the time elapsing between the formation of the liquid composition of the (a) step, and the spray-processing of the same solution in the (b) step is not particularly critical.

In the (b) spraying step of the process of the present invention, the liquid composition, prepared in the (a) step, is sprayed, under the action of a hot gas, through a nozzle, on previously formed solid particles of calcium-urea nitrate, kept moving, preferably inside a revolving drum, and under the action of a gas stream, in particular of air.

The temperature of the liquid stream fed to the nozzles is practically equal to the temperature of formation of the liquid composition.

The temperature of the solid particles may generally vary within the range of from 40° C. to approximately 100° C., and preferably of from 40° to 75° C.

During the treatment of the (b) step of the process, water fed together with the liquid composition is removed, or substantially removed.

According to a form of practical embodiment of the present invention, the cooling of the so-formed particles of calcium-urea nitrate is completed by means of a gas stream inside a second revolving drum, connected in series to the first one.

An end step of post-drying of calcium-urea nitrate particles can be provided for, which performs the task of further enhancing the physical characteristics.

By operating according to the present invention, calcium-urea nitrate can be obtained in the form of a granular and free-flowing solid (of spheroidal shape), with a granulometry of the order of from 2 to 4 mm, free from dusts and from the tendency to release dusts.

When raw materials having the above detailed impurities are used, obtained calcium-urea nitrate has a composition which is generally comprised within the following ranges of values (as percentages by weight):

Urea: 55.3–58.8 %
Calcium nitrate: 37.4–40.6 %
Ammonium nitrate: 2.61–2.84%
Biuret: $\leq 1.2\%$
Total nitrogen content: 34.14–35.14%
Nitric nitrogen content: 6.84–7.43%
Free urea: 0–4.1%
Free calcium nitrate: 0–2.84%
Calcium-urea nitrate content: 92.1–96.07%

A typical calcium-urea nitrate composition which can be obtained according to the present invention is the following:

Urea: 57.05% by weight
Calcium nitrate: 39.02% by weight
Ammonium nitrate: 39.73% by weight
Water: 0.2% by weight
Biuret: 1% by weight The process according to the present invention eliminates the need of operating with an urea excess, and makes it possible a calcium-urea nitrate to be produced, which is endowed with excellent mechanical characteristics, in particular those relating to the hardness of the granules.

Furthermore, the process of the present invention eliminates the drawbacks deriving from phenomena of undercooling of molten calcium-urea nitrate. In our opinion, this desirable result depends on the particular modalities according to which the (b) step of the process is carried out.

According to the process of the present invention, in the preparation of the liquid composition (the (a) step), calcium nitrate in the form of a dry powder, or in the form of a partially dehydrated powder, or in the form of an aqueous suspension with a water content of up to values of the order of 15–18% by weight, can be used. Calcium nitrate is normally available in the form of a concentrated aqueous suspension, obtained by means of the attack of limestone with nitric acid, and subsequent concentration.

Such a suspension has a water content of the order of 15–18% by weight, and an ammonium nitrate content of the order of 5–6% by weight. Its solidification temperature is of approximately 90° C. Its specific gravity is of approximately 1.96 g/ml, and its viscosity at 130° C. is of the order of 110 cst.

According to a form of practical embodiment of the present invention, such an aqueous suspension of calcium nitrate, or similar aqueous suspensions, are directly used for preparing the liquid composition in the (a) step.

According to another form of practical embodiment of the present invention, said suspension is preliminarily submitted to a drying process in order to separate calcium nitrate as a dry powder. For such purpose, the suspension is heated to a temperature of the order of 135° C. and is then sprayed through spray nozzles located at the top of a drying tower. The droplets, falling down towards the bottom of the tower, meet a hot air stream, fed at a temperature which is typically of the order of 300°–350° C., which makes water evaporate from the interior of the droplets towards the outside thereof. That causes free-flowing, hollow granules (bulk density of the order of 0.6–0.8 kg/l) to be formed, which have a very large contact surface area, and are therefore particularly suitable for dissolving into molten urea.

Water evaporation during the drying treatment makes it possible the temperature of the granule (temperature lower than 100° C.) to be reliably controlled. In this way, no appreciable alterations occur in ammonium nitrate content, which is nearly maintained in the dried product. After this treatment, the residual water content in the solid is of the order of 1% by weight.

Suitable equipment for the above disclosed drying process step is constituted by drying towers, provided, at their top, with radially located spray nozzles, and, at their bottom, with a system for hot air feeding.

According to another form of practical embodiment of the present invention, the aqueous suspension of calcium nitrate undergoes a partial drying, in order that a partially dehydrated calcium nitrate powder may be obtained. For that purpose, the suspension, heated at a temperature of the order of 200°–250° C. is sprayed into a vacuum vessel, with the flash effect being taken advantage of, which can be obtained from the vacuum combined with the temperature of the fed stream, in order to partially evaporate water, and obtain calcium nitrate as a partially dehydrated powder (residual water content of the order of 6% by weight), to be used in the formation of the liquid composition of the (a) step of the present process.

This partial drying treatment can be accomplished inside a drying tower of the hereinabove disclosed type.

additionally equipped with a suitable system for maintaining the desired vacuum level (normally of the order of 60 mm$_{Hg}$) and with a system for dumping the separated steam (barometric condenser and vacuum pumps).

According to the process of the present invention, calcium nitrate in dry-powder form, or in the form of a partially dehydrated powder, or as a concentrated aqueous suspension, is mixed with molten urea, with a molar ratio of urea to calcium nitrate of, or approximately of, 4/1, by operating at a temperature comprised within the range of from 100° to 170° C., in order to form a liquid composition containing from 0 to 15% by weight of water.

For that purpose, commercial urea, which may contain up to approximately 1.2% by weight of biuret, can be molten and homogenized with calcium nitrate, with water concentration, when water is present, being adjusted to the desired value. Obviously, in case calcium nitrate is used in the form of a concentrated aqueous suspension, urea at its maximum concentration will be used, so as to keep water content in the liquid composition within the previously detailed range of values.

A too high water content (higher than 8% by weight) in the composition would make it necessary an excessively large amount of water to be evaporated off in the (b) step of the process, that is undesired.

In case calcium nitrate is used as a dry powder, or as a partially dehydrated powder, on the contrary urea at a lower than maximum concentration may be used.

When the process is run with calcium nitrate in the form of a dry or partially dehydrated powder, this reactant is contacted and homogenized with molten urea, with water content in the composition being preferably maintained at values of the order of 1-2% by weight. Under these conditions, the process is advantageously carried out at temperatures comprised within the range of from 145° to 165° C., and the relevant dissolution and calcium-urea nitrate formation times are of the order of a few minutes (for example, of from 3 to 5 minutes), when an efficient homogenizer is used.

When the process is carried out by starting from calcium nitrate in the form of a concentrated aqueous suspension, preferably this reactant, heated at a temperature of at least 130° C., is added to concentrated and molten urea at a temperature slightly higher than approximately 138° C.

In this case too, a quick dissolution is obtained of calcium nitrate into molten urea and, on considering the exothermicity of the reaction, a liquid composition at a temperature of the order of 140°–150° C. is obtained.

The equipment used for forming the liquid composition in the (a) step of the process of the present invention can be any equipment which makes it possible an efficacious and quick homogenization of molten urea and calcium nitrate to be obtained.

In the preferred form of practical embodiment, a reactor is used, which is equipped with a stirrer/-homogenizer which enables a recycle of the material to be maintained inside the reactor. This reactor can be located immediately at the foot of the drying tower, when calcium nitrate in the form of a dry or partially dehydrated powder is used. However, a storage of calcium nitrate leaving this drying tower and its conveyance to a separate section for forming the liquid composition can be provided for.

The liquid composition obtained from the (a) step of the process of the present invention is sprayed, through spray nozzles, on solid particles of calcium-urea nitrate kept moving and under cooling conditions.

In the preferred form of practical embodiment, the liquid composition at a temperature equal to, or approximately equal to, the temperature at which it is formed, is sprayed through nozzles fed with hot air, on a set of curtains of the previously formed solid product, by operating inside a revolving drum, performing the function of agglomerator. The cooling of the solid takes place by using dried air, blown against the curtains of solid product wherein the granules are growing.

The temperature of the gas fed to the nozzle will be a function of the amount of water contained in the composition, and may vary within a range of from about 150° to about 220° C.

The temperature of the granules will be generally maintained at values comprised within the range of from 40° to approximately 100° C. However, in case liquid compositions richer in water are sprayed, the temperature of the granular solid shall not exceed a value of approximately 120° C., in order to prevent phenomena of softening of the same granule. The preferred value for the temperature of the granules is of the order of from 40° to 75° C.

The operation in the (b) step of the process of the present invention can be defined as a "film drying", which enables the granule to grow, with a free-flowing spheroidal shape being given to it.

According to a preferred form of a practical embodiment, the cooling of the granular solid is completed inside a second revolving drum (or a second agglomerator), connected in series to the first one, into which cold and dry air is injected on the rolling curtains, so as to further lower the temperature of the solid.

The so-cooled granules are sieved in order to separate the granules having the desired size (from 2 to 4 mm) from the finer granules, which are directly recycled, and from the coarse granules, which are recycled after a preliminary milling.

A step of post-drying of the so separated granules can be provided for, in order to reach optimum hardness values. Also the use of a hardener agent can be provided for.

The suitable equipment for carrying out the above disclosed operations is preferably as follows.

In the spray operation, a revolving agglomerator is used, which has a drum shape, and is positioned with its generatrix being inclined relatively to the horizontal. The drum is equipped with a system which enables it to revolve around its axis, and bears, at its end, two stationary heads. On its inner surface, devices are located, which make it possible a curtain of granules to be obtained, wherein the granules, on which the dispersion of molten calcium-urea nitrate impinges, which is sprayed through the spray nozzles, grow, without causing, under the above detailed conditions, the phenomenon of undermelting, typical of other granulation techniques, to occur.

Inside the drum, the spray nozzles, fed with air or with another inert gases, are located, which make it possible the dimensions and the shape of the droplets, and of the spray cone as a whole, to be regulated and controlled.

The inclination of the drum gives the stream of particles a helical motion, with the particles leaving from the lowermost portion of the same drum.

The cooling drum is different from the spray drum due to the only fact that it is not provided with spray nozzles. It performs the task of further cooling the solid product, before it leaves.

The sieving device may be of the type which is normally used in the art, and is used in order to select the product leaving the cooling drum, as a function of its granulometry.

As regards the system of conveyance of the solid inside the facility, the granulate is transferred from the spray drum to the cooling drum by gravity, in that the outlet of the first overhangs the inlet of the second drum.

The solid is advantageously recycled to the spray drum by means of a conveyance system of the "air-lift" type, or by means of mechanical lifting devices.

Also devices are provided for, which produce dry air at the necessary temperature for the carrying out the cooling inside the two drums. In particular, when liquid compositions with a low water content are used (in the (a) step), air streams at a relatively low temperature are required. When, on the contrary, the liquid composition contained relatively large amounts of water, higher-temperature air streams are required.

A possible post-drying treatment, destined to further remove residual water from calcium-urea nitrate, can be carried out by delivering hot, dry air through the granules, until the desired humidity removal degree is reached.

According to a form of practical embodiment of the present invention, the hardness of calcium-urea nitrate granules is controlled by adding small amounts of substances, such as, e.g., dolomite, during the preparation of the liquid composition, during the (a) step of the present process.

The process according to the present invention is now illustrated by referring to the FIGURE of the hereto attached drawing table.

More particularly, in said FIGURE by the reference numeral (10) the feed line is indicated, by means of which the concentrated aqueous suspension of calcium nitrate is fed to the drying tower (12) through the spray nozzle (11). By means of the line (13), to the tower (12) an air stream is fed, which is previously heated inside the furnace (14). The top of the tower (12) is connected with the cyclone (15). In the form of practical embodiment wherein vacuum is used, the tower (12) is connected, through the line (16), with the barometric condenser (17), into which water is injected by means of the line (18). By the reference numeral (19), the line is indicated, which is connected with the vacuum source.

At the bottom of the tower (12), by means of the line (20), calcium nitrate is collected in the form of a dry powder or of a partially dehydrated powder, and is sent to the homogenizer (22) after being metered in (21).

To the homogenizer (22) also molten urea is sent by means of the line (23). Inside the homogenizer (22) the liquid composition is formed, which is sent, through the line (24), to the revolving drum (25), through the nozzles (26). Into the revolving drum (25), through the line (27), also an air stream is sent, which is obtained by mixing hot air (line 30) and cold air (line 29) previously dried inside the drier (28).

Exhausted air leaves the drum (25) through the line (31) and is discharged, after a preliminary passage through the filter (32). The granular solid goes, by gravity (33), from the drum (25) to the revolving drum (34).

To the drum (34) a stream of cold and dry air is fed through the line (35), and an exhausted air stream is discharged through the line (36).

The cooled solid is discharged from the drum (34) through the line (37) and is sieved through (38). The fine products are recycled to the drum (25) by means of the line (39). The coarse products are drawn by means of the line (40), are ground in (41), and are recycled through the line (42). The solid having the desired granulometry is drawn through the line (43), and is collected after a possible post-treatment in (44) with a stream of hot air fed through the line (45).

The following experimental examples are illustrative and not limitative of the purview of the present invention.

EXAMPLE 1

Inside the tower, an aqueous solution of calcium nitrate containing 18% by weight of water, 6% of ammonium nitrate and approximately 76% of $Ca(NO_3)_2$ is sprayed.

The hot air used as the drying air is fed to the bottom of the tower at the temperature of 330° C.

The product is a calcium nitrate powder which has the following composition:
water: 1–1.5% by weight
ammonium nitrate: 1–2% by weight
calcium nitrate: 98–96.5% by weight A mixture of anhydrous calcium nitrate powder, molten urea, with added water, is prepared.

Molten urea entering the mixer has the following characteristics:
$H_2O$: 0.5–0.3% by weight
urea: 96.9–97.6% by weight
biuret: 2.6–2.1% by weight The water added from the outside to the mixture represents 2.3% by weight of the molten mixture.

A sample drawn from the molten mixture shows the following composition:
$H_2O$: 1.13–2.21%
biuret: 1.4–1.68%
calcium nitrate: approximately 39.4%
nitric N: 6.7–6.97%
total N: 34.8%

The mixture is fed, through the metering pump, to the first revolving agglomerator, and is sprayed at the temperature of approximately 145° C., with the flow rate and the temperature of compressed air fed to the nozzles, and the flow rate and the temperature of the cooling air being regulated.

The product leaving the growth granulator (at approximately 55° C.) goes to the second cooling drum, then to the sieving system, which separates the finished product (diameter larger than 2 mm) from the product which must still grow.

For a total spraying flow rate of 615 kg/h, a flow rate of 615 kg/h of end product is obtained, with an inner recycle between the two drums of about 1,230 kg/hour.

The end product is granular, with a specific gravity of approximately 1,000 g/liter, suitable for being sacked and used as such as a granular, nitrogenous fertilizer.

The characteristics of the end product are:
diameter of the granule: 2–4 mm
hardness: 600–900 g
$H_2O$: 0.9%
calcium-urea nitrate: 97%
biuret: 1.75%
nitric N: 6.7–6.97%
total N: 34.8%

EXAMPLE 2

A mixture of calcium nitrate and urea, with the addition of $H_2O$ and dolomite is prepared.

The content of calcium nitrate is of 40.5% by weight.
The content of urea is of 47.6% by weight.
The content of dolomite and water is respectively of 4% and 8% by weight.

The nitrate is composed by: $H_2O$ (18%), ammonium nitrate (approximately 6%) and $Ca(NO_3)_2$ (approximately 76%).

Urea is composed by 99.5% of urea, and 0.5% of $H_2O$.

The temperature of the mixture is increased to about 100° C.: at that temperature, the mixture is molten and free-flowing.

The mixture is fed, by means of a centrifugal pump, to the first revolving agglomerator, and is sprayed at the temperature of approximately 100° C., with the temperature and the flow rate of air fed to the nozzles, and the flow rate and the temperature of hot air used as the drying air being regulated.

This latter when leaving the inner distribution manifold of the agglomerator drum, is of about 200° C. The temperature of the bed of granules on which the mixture is sprayed remains around 55°-65° C.

From the growth granulator, the product goes to the second cooling drum, then to the sieving system.

For a total spraying flow rate of about 50 kg/hour, a flow rate of end product of 50 kg/hour is obtained, with an inner recycle of approximately 200 kg/hour.

The analysis of the end product leaving the sieving system supplies the following results:

| ANALYSIS | ∅ 3-4 mm, % | ∅ 4-5 mm, % |
|---|---|---|
| Total N | 32.8 | 32.7 |
| Ureic N | 24.98 | 24.94 |
| $NH_4NO_3$ N | 1.03 | 1.06 |
| $Ca(NO_3)_2$ N | 6.48 | 6.51 |
| Biuret N | 0.32 | 0.30 |
| Calcium | 9.29 | 9.32 |
| Urea | 53.54 | 53.45 |
| $NH_4NO_3$ | 2.96 | 3.02 |
| $Ca(NO_3)_2$ | 38.00 | 38.16 |
| Biuret | 0.78 | 0.75 |
| Water | 1.13 | 1.18 |
| Insolubles in $H_2O$ | 3.96 | 4.07 |
| Hardness | 300 g | 365 g |
| AFTER AIR DRYING FOR 16 HOURS AT 120° C. | | |
| Total N | 32.9 | 32.9 |
| Ureic N | 24.98 | 25.06 |
| $NH_4NO_3$ N | 1.01 | 1.01 |
| $Ca(NO_3)_2$ N | 6.64 | 6.58 |
| Biuret N | 0.34 | 0.32 |
| Calcium | 9.51 | 9.43 |
| Urea | 53.54 | 53.70 |
| $NH_4NO_3$ | 2.89 | 2.88 |
| $Ca(NO_3)_2$ | 38.94 | 38.61 |
| Biuret | 0.83 | 0.80 |
| Water | 0.29 | 0.24 |
| Insolubles in $H_2O$ | 4.8 | 5.01 |
| Hardness | 2150 g | 2500 g |

We claim:

1. A process for the production of calcium-urea nitrate as a granular, free-flowing solid free from the tendency of forming dust, comprising:

(a) preparing a liquid composition containing urea nitrate and calcium nitrate in a molar ratio of about or equal 4:1 at a temperature not greater than 170° C., said composition having a water content ranging from 0 to 15% by weight;

(b) spraying said liquid composition under pressure of a hot gas and at a temperature equal or about equal to its temperature of formation through spray nozzles provided within a revolving drum onto moving solid particles of calcium-urea nitrate within the drum, which particles are at a temperature of 40° to about 100° C., the salt particles within the drum being under a stream of gas; and (c) recovering calcium-urea nitrate from the solid product within the drum.

2. The process according to claim 1, wherein, in step (a) said liquid composition is at a temperature ranging from 100° to 170° C. with the water content of the composition ranging from 0 to 8% by weight, while, in step (b), the calcium-urea nitrate particles are kept moving within said drum at a temperature ranging from 40° to 75° C. with cooling of the particles within the drum being accomplished by the flow of a stream of air.

3. The process of claim 1, wherein, in step (a), said calcium-urea nitrate reactant is in the form of a dry powder obtained by drying a concentrated aqueous suspension of calcium nitrate with a flow of hot air within a tower.

4. The process of claim 1, wherein, in step (a), said calcium nitate reactant is employed in the form of a partially dehydrated powder obtained by dehydrating a concentrated aqueous suspension of calcium nitrate within a vacuum vessel.

5. The process of claim 1, wherein, in step (a), the calcium nitrate reactant employed is in the form of a concentrated aqueous suspension of calcium nitrate having a water content within the range of 15 to 18% by weight.

6. The process of claim 1, wherein, in step (a), said calcium nitate reactant contains up to about 5 to 6% by weight of ammonium nitrate.

7. The process of claim 1, wherein, in step (a), the urea from which said urea nitrate reactant is prepared contains up to about 1.2% by weight of biuret.

8. The process of claim 1, wherein, in step (a), said calcium nitrate reactant is homogenized and dissolved in molten urea at a temperature within the range of from 100° to 170° C. within a time of about 3 to 5 minutes.

9. The process of claim 8, wherein the operations of homogenization and dissolution are conducted within a stirred reactor equipped with an inner recycle.

10. The process of claim 1, wherein, in step (b), the solid particles of calcium-urea nitrate obtained by said spraying operation are cooled by means of a stream of cold air.

11. The process of claim 10, wherein the particles of calcium-urea nitrate are further cooled within a revolving drum.

12. The process of claim 1, wherein the solid particle product of calcium-urea nitrate obtained is further dried by contacting the particles with a stream of hot air.

13. The process of claim 1, wherein the hardness of the calcium-urea nitrate particulate product obtained is regulated by the controlled addition of small amounts of a hardening regulating substance to the liquid composition of step (a).

14. The process of claim 3, wherein said hardening regulating substance is dolomite.

* * * * *